(12) United States Patent
Baum et al.

(10) Patent No.: US 9,037,219 B2
(45) Date of Patent: May 19, 2015

(54) ESTIMATION OF DISTANCES AND SIZE OF LESIONS IN THE COLON WITH AN IMAGING CAPSULE

(75) Inventors: Gideon Baum, Haifa (IL); Yoav Kimchy, Haifa (IL)

(73) Assignee: CHECK-CAP LTD., Isfiya (IL)

( * ) Notice: Subject to any disclaimer, the term of this patent is extended or adjusted under 35 U.S.C. 154(b) by 121 days.

(21) Appl. No.: 13/825,018

(22) PCT Filed: Sep. 22, 2011

(86) PCT No.: PCT/IL2011/000749
§ 371 (c)(1),
(2), (4) Date: Mar. 19, 2013

(87) PCT Pub. No.: WO2012/038960
PCT Pub. Date: Mar. 29, 2012

(65) Prior Publication Data
US 2013/0197360 A1    Aug. 1, 2013

Related U.S. Application Data

(60) Provisional application No. 61/344,731, filed on Sep. 23, 2010.

(51) Int. Cl.
| | |
|---|---|
| *A61B 5/107* | (2006.01) |
| *A61B 5/07* | (2006.01) |
| *A61B 6/00* | (2006.01) |
| *A61B 1/00* | (2006.01) |
| *A61B 1/04* | (2006.01) |
| *A61B 1/31* | (2006.01) |
| *A61B 5/00* | (2006.01) |
| *A61M 31/00* | (2006.01) |

(52) U.S. Cl.
CPC .............. *A61B 5/1076* (2013.01); *A61B 5/073* (2013.01); *A61B 6/4057* (2013.01); *A61B 6/481* (2013.01); *A61B 6/483* (2013.01); *A61B 6/485* (2013.01); *A61B 6/547* (2013.01); *A61B 1/00016* (2013.01); *A61B 1/041* (2013.01); *A61B 1/043* (2013.01); *A61B 1/31* (2013.01); *A61B 5/4255* (2013.01); *A61B 5/7278* (2013.01); *A61B 6/425* (2013.01); *A61M 31/005* (2013.01)

(58) Field of Classification Search
CPC .... A61B 1/00016; A61B 1/041; A61B 1/043; A61B 1/31; A61B 5/073; A61B 5/1076; A61B 5/4255; A61B 5/7278; A61B 6/4057; A61B 6/425; A61B 6/481; A61B 6/483; A61B 6/485; A61B 6/547; A61M 31/005
See application file for complete search history.

(56) References Cited

U.S. PATENT DOCUMENTS

| | | | |
|---|---|---|---|
| 2009/0318760 A1* | 12/2009 | Pascal et al. ................... | 600/117 |
| 2010/0272318 A1* | 10/2010 | Cabiri et al. ................... | 382/106 |

FOREIGN PATENT DOCUMENTS

| | | |
|---|---|---|
| WO | WO 2005/058129 | 6/2005 |
| WO | WO 2008/096358 | 8/2008 |

*Primary Examiner* — Ruth S Smith
(74) *Attorney, Agent, or Firm* — Soroker—Agmon (57) ABSTRACT

A method of estimating distances in a colon of a subject, including: orally administering to a subject a contrast agent, orally administering an imaging capsule to the subject, emitting radiation from the imaging capsule at a location in the colon, detecting photons that are returned from an interaction of the radiation with an inner wall of the colon and contents of the colon, summating the detected photons with energies corresponding to X-ray fluorescence interactions to form a first count, summating the detected photons with energies corresponding to Compton back-scattering interactions to form a second count, determining the distance from the imaging capsule to the inner wall of the colon and a concentration of the contrast agent at the location of the imaging capsule in the colon using the values of the first count and the second count.

12 Claims, 7 Drawing Sheets

ESTIMATION OF DISTANCES AND SIZE OF LESIONS IN THE COLON WITH AN IMAGING CAPSULE

RELATED APPLICATIONS

The present application claims priority from U.S. Provisional application No. 61/344,731 filed on Sep. 23, 2010, the disclosure of which is incorporated herein by reference.

TECHNICAL FIELD

The present disclosure relates generally to imaging the insides of a patient's colon using an intra-lumen imaging capsule and more specifically to estimating the distance from the capsule to the internal walls of the colon and estimating the size of lesions thereof.

BACKGROUND

One method of examining the gastrointestinal tract for the existence of polyps and other clinically relevant features that may provide an indication regarding the potential of cancer is performed by swallowing an imaging capsule that will travel through the entire gastrointestinal (GI) tract and view the patient's situation from the inside. In a typical case the trip can take between 24-48 hours, after which the imaging capsule exits in the patient's feces. Typically the patient swallows a contrast agent to enhance the imaging ability of the imaging capsule. Then the patient swallows the imaging capsule to examine the gastrointestinal tract while flowing through the contrast agent. The imaging capsule typically includes a radiation source, for example including a radioisotope that emits X-rays or Gamma rays. The radiation is typically collimated to allow it to be controllably directed in a specific direction during the imaging process. In an exemplary case the imaging capsule is designed to measure Compton back-scattering and transmits the measurements (e.g. count rate) to an external analysis device, for example a computer or other dedicated instruments.

In a typical implementation a radio-opaque contrast agent is used so that a position with a polyp will have less contrast agent and will measure a larger back-scattering count to enhance accuracy of the measurements. Alternatively, other methods may be used to image the gastrointestinal tract.

U.S. Pat. No. 7,787,926 to Kimchy, the disclosure of which is incorporated herein by reference, describes details related to the manufacture and use of such an imaging capsule.

One challenge in estimating the distance from the imaging capsule to the inner walls of the colon is that the measurements are affected by the radiation blocking ability of the contents surrounding the imaging capsule: generally the contrast agent. The blocking ability of the contrast agent is dependent on the concentration of the contrast agent. Generally the patient can swallow a contrast agent of a specific concentration, however while advancing through the GI tract the water contained in the colon contents is absorbed by the colon leaving a less diluted solution have a higher concentration of contrast agent surrounding the imaging capsule. Additionally in some cases the patient is required to drink more contrast agent at specific times to assure proper functionality of the imaging capsule. Therefore at any specific position the concentration is not known. As a result the distance measurements may not be accurate as desired.

There is thus a need for improved methods of measuring the distance from the imaging capsule to the walls of the colon.

SUMMARY

An aspect of an embodiment of the disclosure relates to a system and method for measuring distances inside a patient's colon and optionally using the measurements to construct an image of the inside of the colon. The patient swallows a radio opaque contrast agent and then swallows an imaging capsule. The imaging capsule emits radiation at its current location in the colon and then detects photons that are returned from interactions of the radiation with an inner will of the colon and the contents of the colon, for example the contrast agent.

Two types of interactions with the radiation produce most of the returned photons:
1. X-ray fluorescence;
2. Compton back-scattering.

The photons of each type of interaction have specific ranges of energy and can be identified by the energy level of the detected photons. The system counts the photons for each energy level and then summates the photons with energy levels corresponding to X-ray fluorescence interactions to form a first count and the photons with energy levels corresponding to Compton back-scattering to form a second count. The first count and second count are then used to determine the distance from the imaging capsule to the inner wall of the colon and to determine the concentration of the contrast agent at the location of the imaging capsule.

In an exemplary embodiment of the disclosure, the emitting and detecting are performed on the entire circumference of the inner wall of the colon at the location of the imaging capsule. Optionally, the emitting and detecting are performed repeatedly along the length of the colon as the imaging capsule progresses.

in an exemplary embodiment of the disclosure, the information from the detecting is transmitted wirelessly to an external processing device (e.g. a computer) having a program that handles the information. Optionally, the external computer counts the photons according to their energy level and summates them according to the type of interaction that they initiated from. Alternatively, the imaging capsule may summate the photons according to the type of interaction and transmit the results to the computer.

In an exemplary embodiment of the disclosure, the determined distances are used to determine the size and location of polyps inside the colon and to construct images of the inside of the colon.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1A:
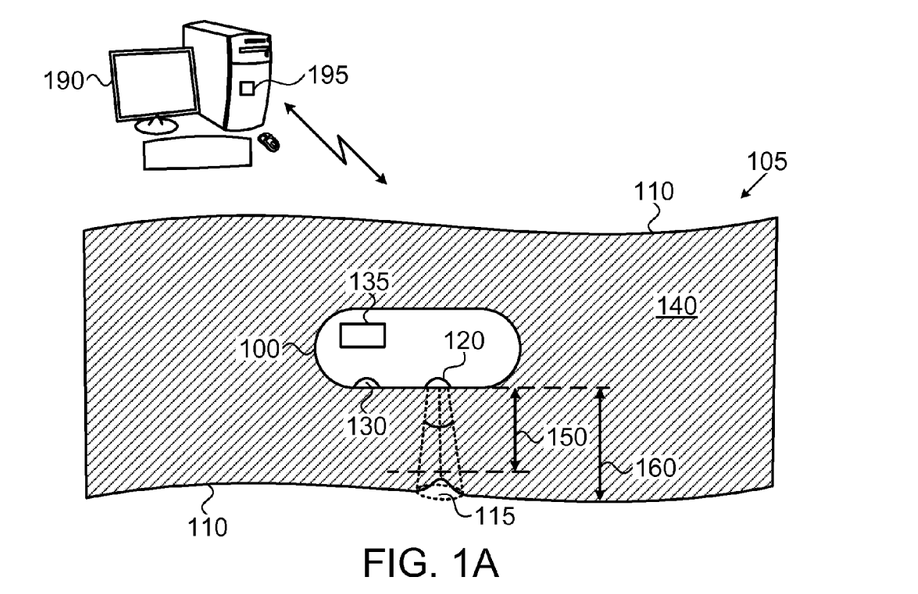
FIG. 1A is a schematic cross sectional side view of an imaging capsule deployed in a patient's colon, according to an exemplary embodiment of the disclosure.
Figure 1B:
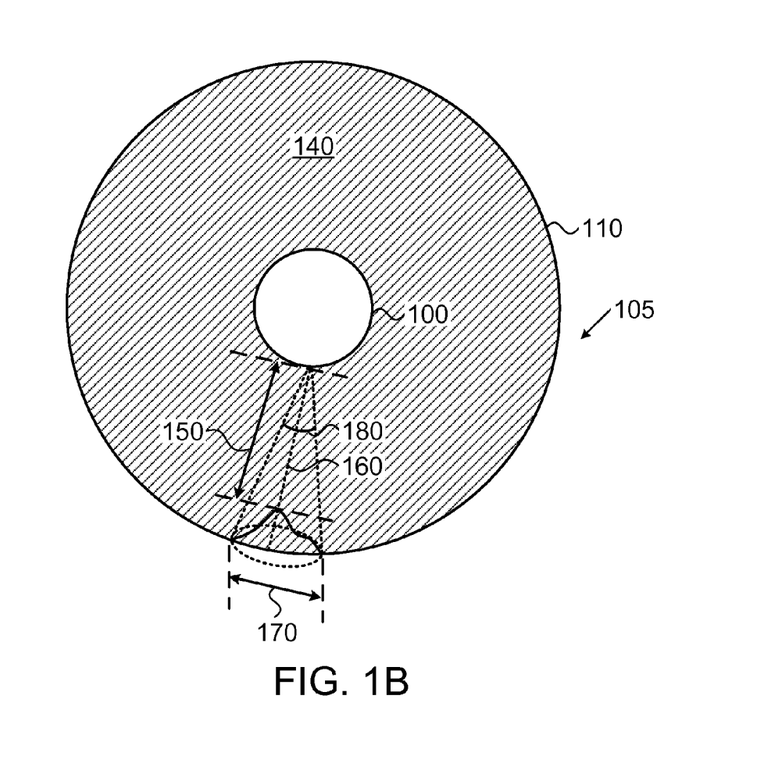
FIG. 1B is a schematic cross sectional view of an imaging capsule deployed in a patient's colon, according to an exemplary embodiment of the disclosure.

FIG. 1A is a schematic cross sectional side view of an imaging capsule 100 deployed in a patient's colon 105, and FIG. 1B is a schematic cross sectional view of an imaging capsule 100 deployed in a patient's colon 105, according to an exemplary embodiment of the disclosure. In an exemplary embodiment of the disclosure, the patient first drinks a contrast agent 140 that mixes with the colon contents. The contrast agent 140 assists in enabling the imaging capsule 100 to perform measurements and form a 3-dimensional image of colon 105 from the inside. Optionally, the contrast agent 140 includes water mixed with a radio opaque material with a relatively high atomic number such as, for example, Barium (atomic number 56) or Iodine (atomic number 53). After drinking the contrast agent 140 the patient swallows imaging capsule 100. Imaging capsule 100 travels through the patient's GI tract and through the colon until it exits in the patient's feces.

In an exemplary embodiment of the disclosure, imaging capsule 100 includes a radiation emitter 120 and a radiation detector 130. In some aspects, the radiation emitter 120 provides a collimated radiation beam that emits radiation while rotating 360 degrees inside imaging capsule 100 to scan the entire inner circumference of the colon walls 110 as the imaging capsule progresses through the colon. In an exemplary embodiment of the disclosure, radiation detector 130 rotates with radiation emitter 120 to detect the photons that are returned from interactions with the emitted radiation. In some aspects, radiation detector 130 may include detectors surrounding the outer circumference of imaging capsule 100 to detect radiation from all sides of imaging capsule 100. in some aspects, radiation detector 130 may he a solid state detector, for example a Cadmium Telluride (CdT1) compound serving as a detector. In an exemplary embodiment of the disclosure, imaging capsule 100 emits X-ray radiation and measures photons returned by two physical phenomenon causing interactions with the radiation. In an exemplary embodiment of the disclosure, the two physical phenomenons are Compton back-scattering and X-ray fluorescence. The measured photons related to these phenomenon are used to determine the distance 160 from imaging, capsule 100 to the surrounding walls 110 of the colon or the distance 150 to polyps 115 extending from the inner walls 110 of the colon 105.

In an exemplary embodiment of the disclosure, imaging capsule 100 includes a transmitter 135 (e.g. an RF transmitter) to transmit the measurements to an external processing device 190 for processing. In an exemplary embodiment of the disclosure, processing device 190 is a general purpose computer with an executable program 195 that accepts the measurements from the imaging capsule 100. Optionally, program 195 determines the distances (e.g. 150 and 160) inside colon 105 and constructs a 3 dimensional image of the colon for a medical practitioner to view. Optionally, the processing device 190 also determines the width 170 and height (160-150) of polyps extending from the colon walls 110. In an exemplary embodiment of the disclosure, imaging capsule 100 travels in the longitudinal direction through the colon. The imaging capsule 100 may be off center sometimes during the journey. In an exemplary embodiment of the disclosure, program 195 compensates for deviations from the center by using the measurements that are performed on the entire circumference inside the colon and adjusting the results if necessary.

In some embodiments of the disclosure, imaging capsule 100 may include an internal processing device and transmit 3-dimensional images directly to an external viewing device for the medical practitioner to view.

In an exemplary embodiment of the disclosure, the radiation emitter emits X-ray radiation, for example between 10 to 100 KeV (e.g. 59.4 KeV). Optionally, the X-ray photons interact with the contrast agent, the contents of the colon and the tissue of the colon walls 110. The interactions cause the return of photons to detector 130 based on two physical phenomenons:

1. Compton back-scattering (CMT)—The X-ray photons emitted from imaging capsule 100 collide with the electrons of the colon content and the tissue of the colon walls 110 and provide back-scattered photons of specific energies, which are detected by detector 130. Additionally, the backscattered photons are attenuated by the distance traveled. The larger the distance that the back-scattered photons travel through the contrast agent 140 the less the number of back-scattered photons that will be detected since the contrast agent enhances absorption of the photons. When a polyp 115 exists on the colon wall 110 the distance is shorter, less contrast agent absorbs the photons and more will he detected by detector 130.

2. X-ray Fluorescence (XRF)—The X-ray photons emitted from the imaging capsule interact with the atoms of the contrast agent and the rest of the contents of the colon 105, The interactions cause ionization, which yields a fluorescent photon flux with specific energy levels from the heavy atoms in the contrast agent such as Iodine or Barium. Additionally, the larger the distance from imaging capsule 100 the more X-ray fluorescence will be detected and the shorter the distance the less X-ray florescence will be detected.

Figure 2:
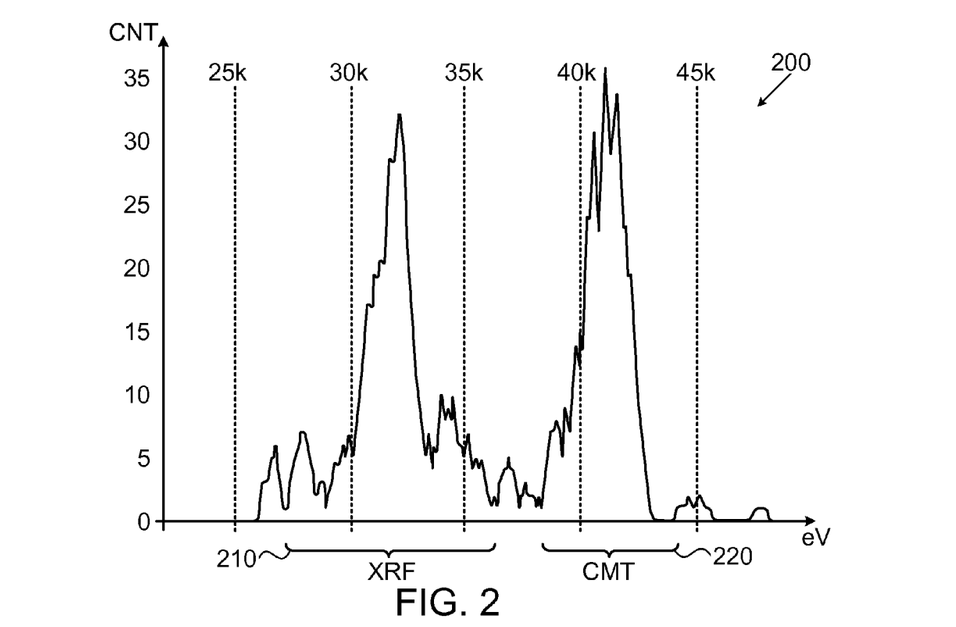
FIG. 2 is a schematic illustration of a graph of a count of detected photons, according to an exemplary embodiment of the disclosure.

The photon energy (KeV) far the photons released by each of the two physical phenomenon is different so the results from each phenomenon can be analyzed independently. FIG, 2 is a schematic illustration of a graph 200 of a count of detected photons, according to an exemplary embodiment of the disclosure. In a. typical case the X-ray fluorescence forms the two highest peaks on the of left side of the graph (lower energies) and the Compton back-scattering forms the highest peak on the right side of the graph (higher energies). The energies of the peaks are generally known since they depend mainly on the energy of the emitted radiation, the compounds in the contrast agent and the geometry between the radiation emitted and the detector's position relative to the emitter.

Figure 3:
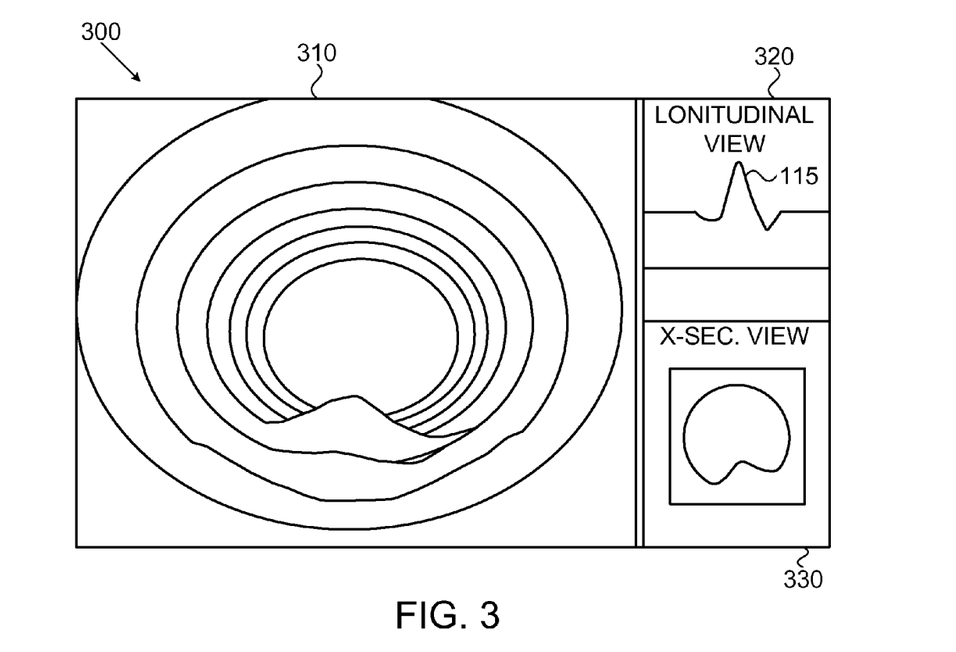
FIG. 3 is a schematic illustration of images of the inside of a colon, according to an exemplary embodiment of the disclosure.

FIG. 3 is a schematic illustration of images 300 of a colon, according to an exemplary embodiment of the disclosure. Image 310 shows a computer reconstructed cross sectional perspective. view of the inside of colon 105 with a polyp 115 on the bottom surface. Image 310 is reconstructed based on the measurements of imaging capsule 100. Image 320 shows a longitudinal side view of the inside of the colon 105 with polyp 115 and image 330 shows a cross sectional view of the colon at the position of the polyp 115.

Figure 4:
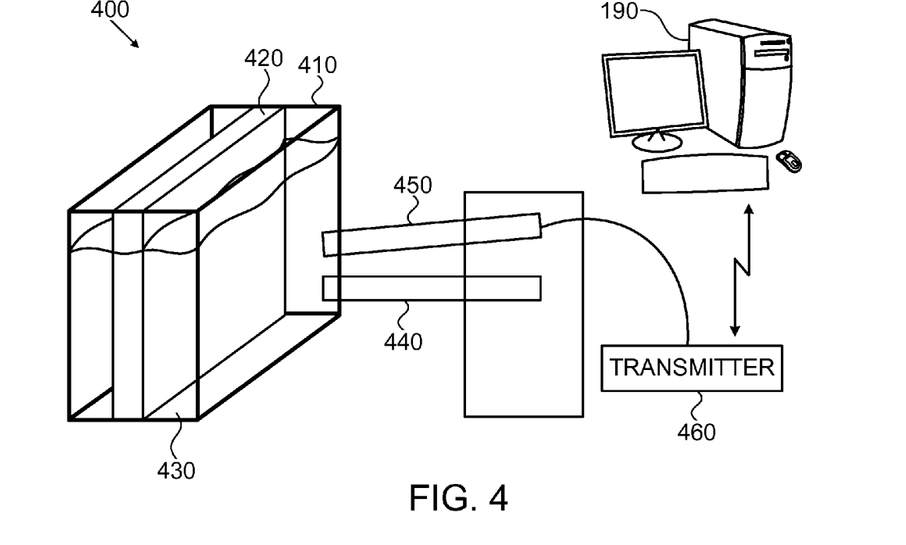
FIG. 4 is a schematic illustration of an experiment demonstrating the calculation of distances in the colon, according to an exemplary embodiment of the disclosure.

Following are details of an experiment 400 conducted to demonstrate the connection between the distances (150, 160 and 170) and the results measured. from Compton back-scattering and X-ray fluorescence as described above. FIG. 4 is a schematic illustration of the setup of experiment 400 to demonstrate the calculation of distances in the colon 105, according to an exemplary embodiment of the disclosure. In an exemplary embodiment of the disclosure, a tank 410 of water mixed with a contrast agent 430 is used to demonstrate colon 105. A slab 420 of plastic with the same density as water is used to demonstrate the colon tissue and the tissues beyond. A collimated radiation source 440 emitting X-ray radiation at 59.4 Key (e.g. using an Am241 radiation source) is used to provide X-ray radiation. A solid state (CdT1) radiation detector 450 counts photons that are released responsive to the X-ray radiation. The measurements are provided to a transmitter 460 that transmits the measurements wirelessly to processing device 190, such as, for example, a computer that executes program 195.

In an exemplary embodiment of the disclosure, slab 420 was positioned at various distances (e.g. 0-30 mm) relative to the radiation source 440 to see the effect on the measurements. Additionally, the measurements were repeated for various concentrations of contrast agent 430, for example 1% -8%. The graph in FIG. 2 shows a typical spectrum with two areas:

1. Area 210 representing the results from X-ray florescence with 2 peaks, for example one large and one smaller between 30 KeV and 35 KeV, and 2. Area 220 representing the results from Compton back-scattering with a peak, for example between 40-45 KeV.

Figure 5:
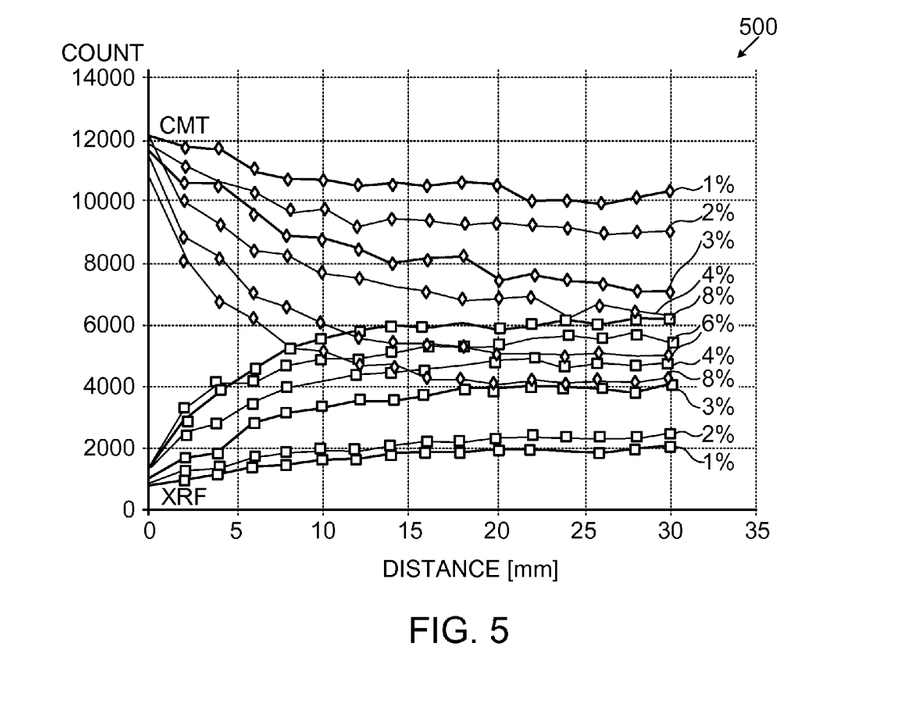
FIG. 5 is a schematic illustration of a graph depicting the experimental results showing the relationship of the photon count, distance from the radiation source and concentration of the contrast agent, according to an exemplary embodiment of the disclosure.

The results of area 210 and area 220 for various distances and contrast agent concentrations were integrated and provided in graphical form. FIG. 5 is a schematic illustration of a graph 500 depicting the experimental results showing the relationship of the photon count, distance from the radiation source and concentration of the contrast agent, according to an exemplary embodiment of the disclosure. The lower lines correspond to X-ray fluorescence and the upper lines correspond to Compton back-scattering. Each line represents a different concentration percentage for various distances. As shown in graph 500 the more concentrated the contrast agent the greater the count the for X-ray fluorescence and the lower the count for Compton back-scattering. Likewise the greater the distance from the radiation source the greater the count for X-ray fluorescence. and the lower the count for Compton back-scattering.

In an exemplary embodiment of the disclosure, program 195 is required m determine the distance L as a function of the counts (I) of the X-ray florescence and Compton back-scattering (i.e. $L=L(I_{CMT}, I_{XRF})$).

Figure 6A:
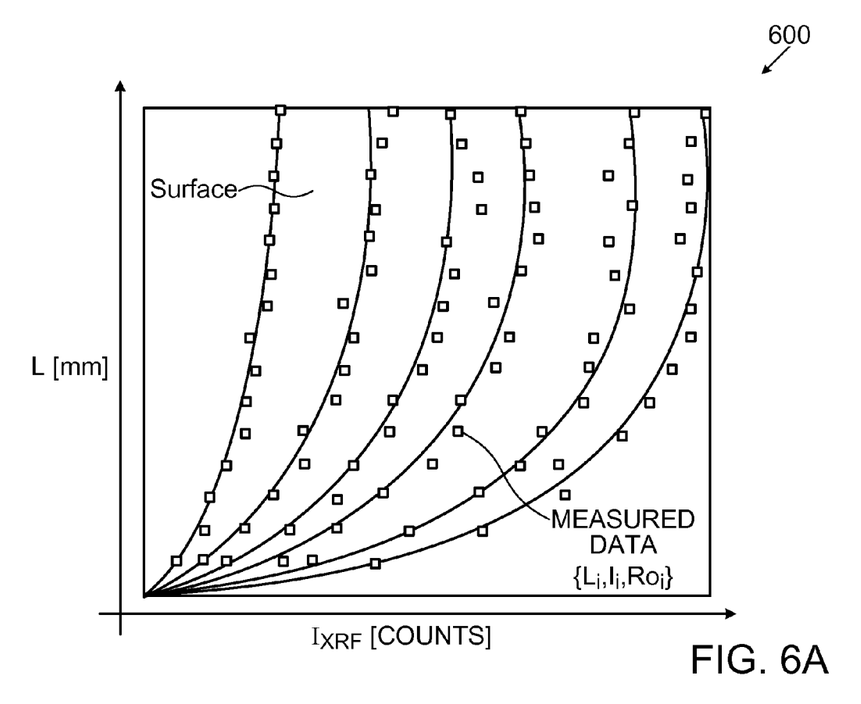
FIG. 6A is a schematic illustration of a graph depicting a surface representing the distance as a function of the count and contrast agent concentration for X-Ray fluorescence, according to an exemplary embodiment of the disclosure.
Figure 6B:
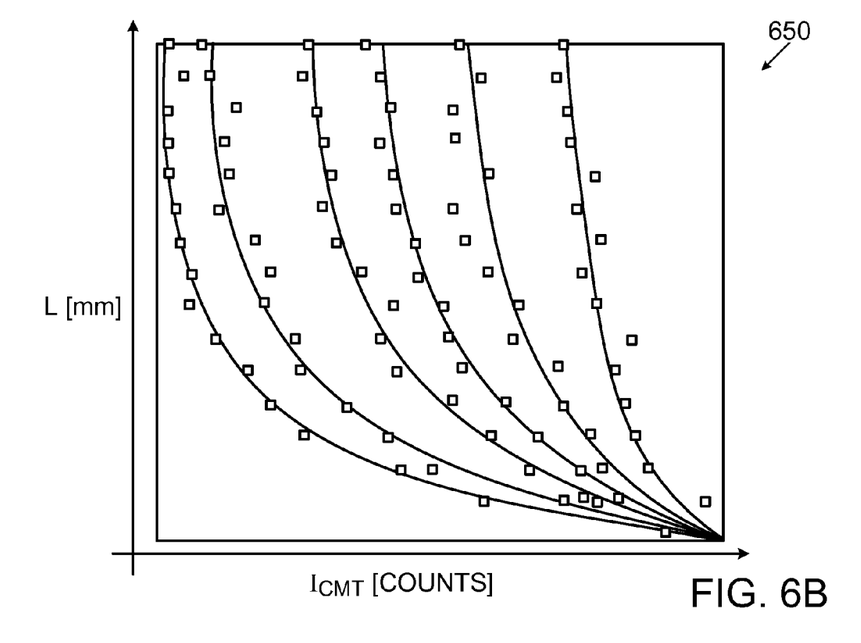
FIG. 6B is a schematic illustration of a graph depicting a surface representing the distance as a function of the count and contrast agent concentration for Compton back-scattering, according to an exemplary embodiment of the disclosure.

FIG. 6A is a schematic. illustration of a graph 600 depicting a surface representing the distance (L) as a function of the count (I) and contrast agent concentration (Ro) for X-Ray fluorescence, and FIG. 6B is a schematic illustration of a graph 650 depicting a surface representing the distance (L) as a function of the count (I) and contrast agent concentration Ro) for Compton back-scattering, according to an exemplary embodiment of the disclosure.

In an exemplary embodiment of the disclosure, for specific count values ($I_{CMT}$, $I_{XRF}$) at a specific moment (when the imaging capsule is at a specific position) a set of 2 functions can be obtained from the surfaces in graphs 600 and 650 providing an estimated distance ($L_{EST}$) as a function o the concentration of contrast agent 430 (a line on the surface representing a specific concentration):

$$L_{EST}=L_{CMT}(Ro, I_{CMT}=\text{constant}); \text{ and}$$

$$L_{EST}=L_{XRF}(Ro, I_{XRF}=\text{constant}).$$

Figure 7:
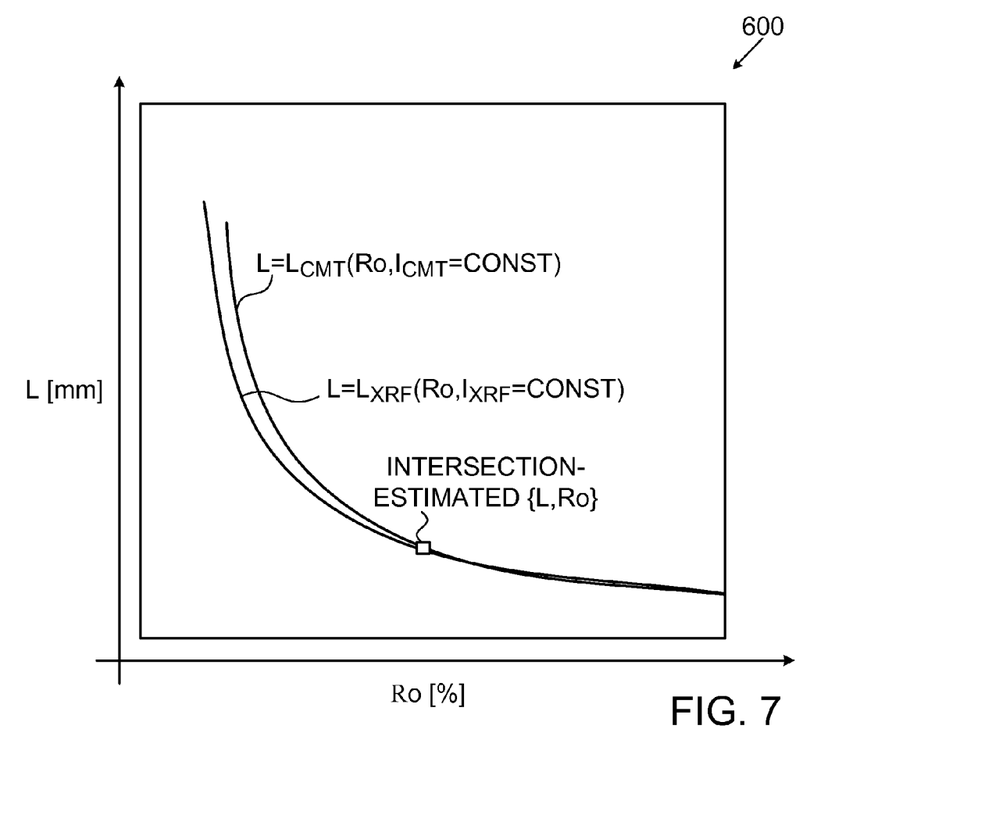
FIG. 7 is a schematic illustration of a graph depicting an estimation of distance and concentration for a specific photon count, according to an exemplary embodiment of the disclosure.

Optionally, program 195 finds the intersection point of the 2 curves yielding the estimated distance $L_{EST}$ and the concentration (Ro). FIG. 7 is a schematic illustration of a graph 700 depicting an estimation of the distance $L_{EST}$ and concentration (Ro) for a specific photon count, according to an exemplary embodiment of the disclosure.

In an exemplary embodiment of the disclosure, during live application of imaging capsule 100 through a patient's colon 105, various disturbances may hinder the calculations described above and disturb the smoothness of the results, for example the concentration of the contrast agent varies throughout the colon 105. Additionally, the concentration is lower at the beginning and increases toward the exit from the colon due to absorption of water from the colon leaving the molecules of the contrast agent at a higher concentration. In order to overcome disturbances the following method and assumptions are used:

1. The contrast agent concentration (Ro) is assumed to change gently along the colon tract.

2. The results of the concentration will be calculated based on the estimation calculations used above.

3. The concentration for a sequence of positions will be filtered by regression to provide a smooth function.

4. The smoothed concentration function will be used to estimate the distance 160 either using the Compton back-scattering curve or the X-ray fluorescence curve (as shown in FIG.7):

$$L_{EST}=L_{CMT}(Ro_{smooth}, I_{CMT}=\text{constant}) \text{ or } L_{EST}= L_{XRF}(Ro_{smooth}, I_{XRF}=\text{constant}).$$

Figure 8A:
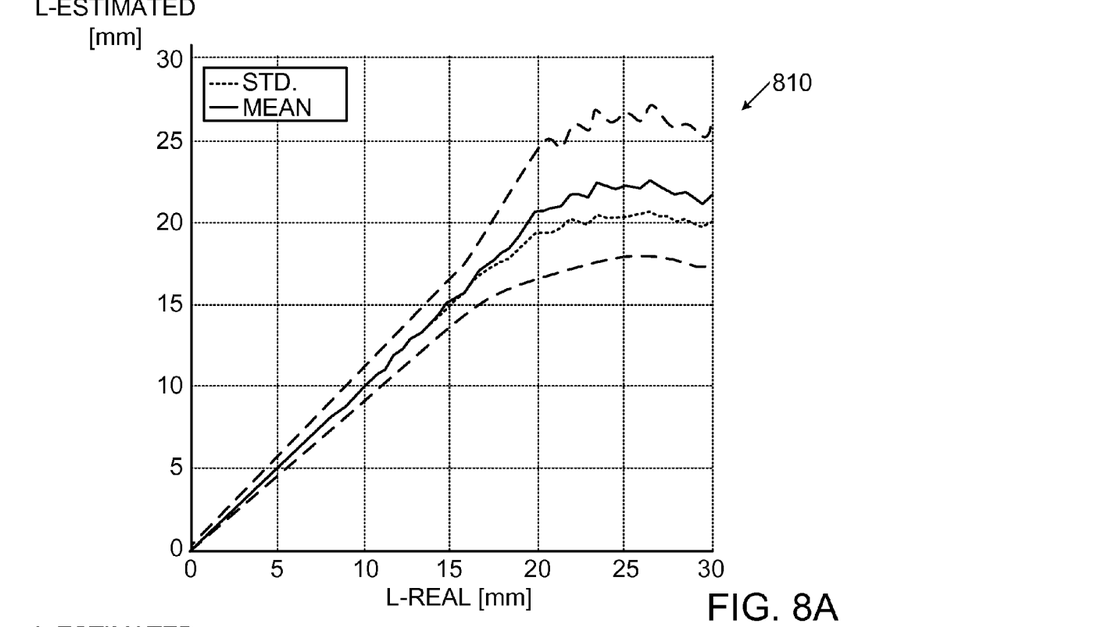
FIGS. 8A, 8B and 8C are schematic graphs that demonstrate the relationship between an estimated distance and a real distance as a function of concentration, according to an exemplary embodiment of the disclosure.
Figure 8B:
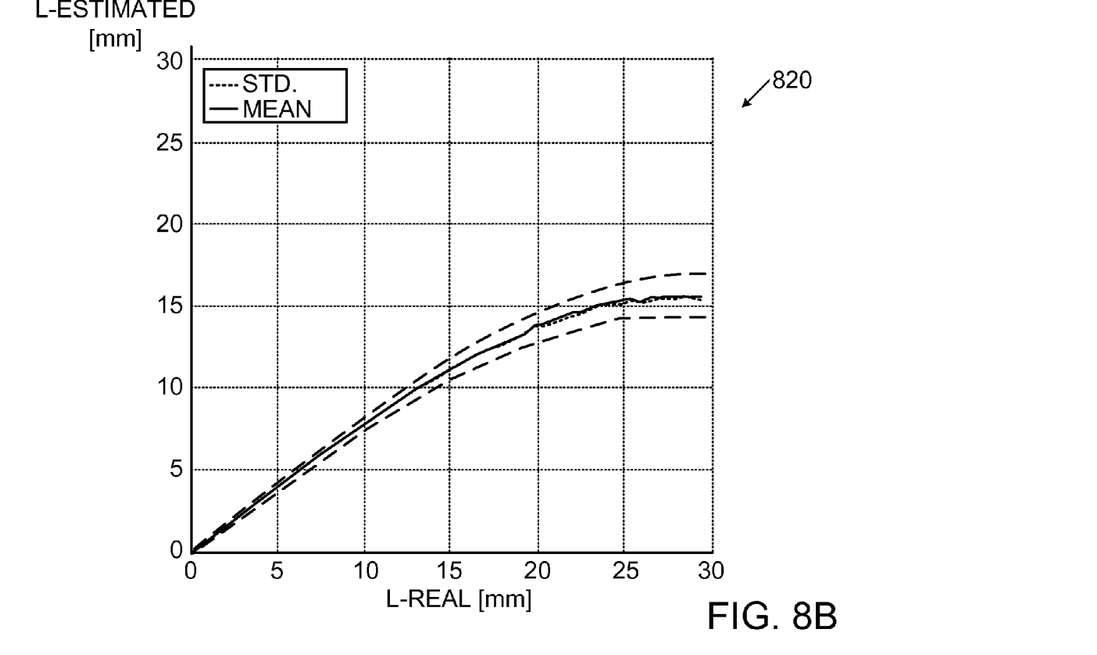
Figure 8C:
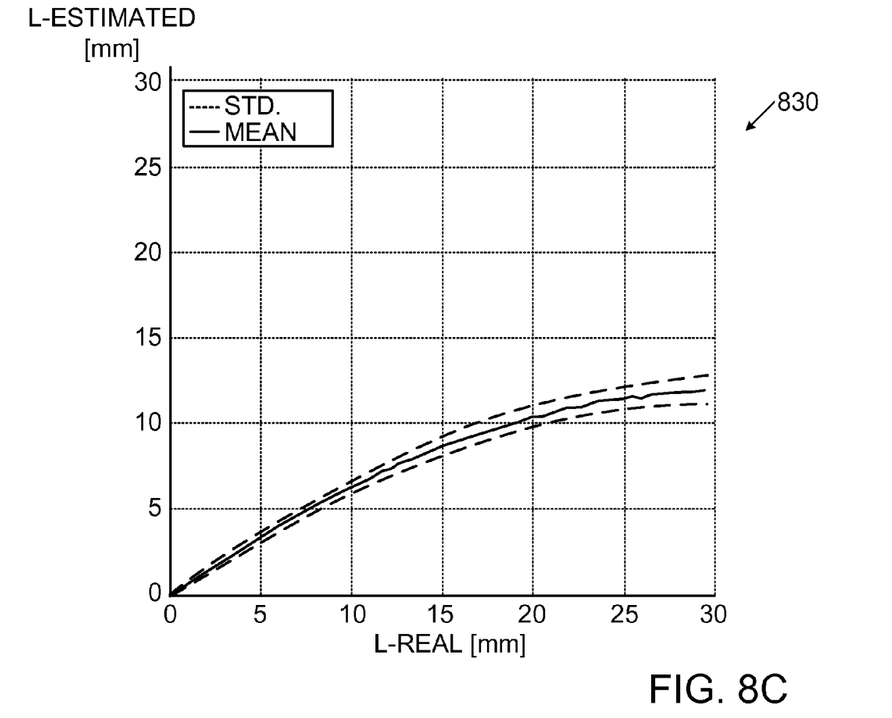

In an exemplary embodiment of the disclosure, the performance of the estimation calculation is evaluated by comparing the estimated distance ($L_{EST}$) to the real ($L_{REAL}$) distance in the experiment described above. FIGS. 8A, 8B and 8C are schematic graphs that demonstrate the relationship between the estimated distance and the real distance as a function of the concentration (Ro). The figures show two dotted outer lines showing the boundaries of the results based on the measurements and two inner lines one showing the standard deviation of the measured results and one showing the mean of the measured results. FIG. 8A shows the relationship for Ro=8%, FIG. 8B shows the relationship for Ro=6% and FIG. 8C shows the relationship for Ro=4%. The results of the graph show that good results can be obtained for distances up to 20 mm with a concentration of 8% and larger distances for lower concentration. Typically imaging capsule 100 will travel along the longitudinal direction, which has a typical diameter of 30-40 mm and a maximum of up to about 50 mm. However it should be noted that during movement, the colon typically contracts to less than 50% of its normal diameter leaving a short distance between the colon wall 110 and imaging capsule 100 in the order of 5-15 mm at the most.

In an exemplary embodiment of the disclosure, after calculating the distance from imaging capsule 100 to the colon walls 110 other measurements may be calculated based on the results. In an exemplary embodiment of the disclosure, the width (D) 170 (FIG. 1B) of a polyp 115 can be estimated by calculating an angle (A) 180 enclosing the polyp 115, for example the angle between two scanning positions during rotation of the radiation source where the length is larger than the length over width D because of the polyp 115 or that the length is substantially the same as the rest of the circumference except over width D. Additionally, geometric calculations can be used to determine the width of polyp 115, for example by calculating $D=2*L*\tan(A/2)$.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure.

It will be appreciated by persons skilled in the art that the present disclosure is not limited to what has been particularly shown and described hereinabove.

We claim:

1. A method of estimating distances in a colon of a subject that is orally administered an imaging capsule and a radio opaque contrast agent so as to fill the colon with the radio opaque contrast agent having a concentration of the contrast agent varying at different locations along a length of the colon, comprising:
    receiving an experimentally predetermined relationship between a number of photons with energies corresponding to X-ray fluorescence interactions, a distance from the imaging capsule to the inner wall of the colon and the concentration of the contrast agent;
    receiving an experimentally predetermined relationship between a number of photons with energies corresponding to Compton back-scattering interactions, the distance from the imaging capsule to the inner wall of the colon and the concentration of the contrast agent;
    receiving an experimentally predetermined relationship between a number of photons with energies corresponding to Compton back-scattering interactions, the distance from the imaging capsule to the inner wall of the colon and the concentration of the contrast agent;
    emitting radiation from an emission source in the imaging capsule at a location in the colon;
    detecting photons that are returned from an interaction of the radiation with an inner wall of the colon and contents of the colon at the location;
    summating ones of said detected photons with energies corresponding to X-ray fluorescence interactions to form a first count;
    summating ones of said detected photons with energies corresponding to Compton back-scattering interactions to form a second count;
    solving for the distance from the image capsule to the inner wall of the colon and the concentration at the location based on the predetermined relationships, the first count and the second count;
    determining distances by solving for the distance from the imaging capsule to the inner wall of the colon on the entire circumference of the colon;
    identifying a polyp from the determined distances;
    calculating an angle enclosing the polyp;
    determining the width of the polyp from the calculated angle and determined distances.

2. A method according to claim 1, wherein said emitting and detecting are performed repeatedly along the length of the colon as the imaging capsule progresses.

3. A method according to claim 1, further comprising wirelessly transmitting information from said detecting to an external processing device.

4. A method according to claim 3, wherein said summating and said determining are performed by the external processing device.

5. A method according to claim 1, further comprising determining the height of polyps inside the colon from a plurality of determined distances between the imaging capsule and the inner wall of the colon.

6. A method according to claim 1, wherein said detecting is performed with a detector that is coupled to the emission source and moves with it inside the imaging capsule.

7. A method according to claim 1, wherein said detecting is performed with a detector that is independent of the emission source.

8. A method according to claim 1, wherein said radiation is X-ray radiation.

9. A system for estimating distances in a colon of a subject that is orally administered a radio opaque contrast agent so as to fill the colon with the radio opaque contrast agent having a concentration of the contrast agent varying at different locations along the length of the colon, comprising:
    (a) an imaging capsule adapted to be swallowed by the subject after oral administration of the radio opaque contrast agent, the imaging capsule comprising:
        a radiation emitter for emitting radiation at a location in the colon;
        a radiation detector adapted to detect photons from interactions of the emitted radiation with an inner wall of the colon and the contents of the colon, the detected photons have energies corresponding to X-ray fluorescence interactions and to Compton back-scattering, interactions; and
        a transmitter adapted to transmit information of the detected photons to a processing device;
    (b) a processing device adapted to:
    receive an experimentally predetermined relationship between a number of photons with energies corresponding to X-ray fluorescence interactions, a distance from the imaging capsule to the inner wall of the colon and the concentration of the contrast agent;
    receive an experimentally predetermined relationship between a number of photons with energies corresponding to Compton back-scattering interactions, the distance from the imaging capsule to the inner wall of the colon and the concentration of the contrast agent;
    summate ones of said detected photons with energies corresponding to the X-ray fluorescence interactions to form a first count and to summate ones of said detected photons with energies corresponding to the Compton back-scattering interactions to form a second count, said processing device being further adapted to solve for the distance from the imaging capsule to the inner wall of the colon and the concentration at the location based on the predetermined relationships, the first count and the second count, determine distances by solving for the distance from the imaging capsule to the inner wall of the colon on the entire circumference of the colon using the values of the first count and the second count; and
    wherein said processing device is adapted to identify a polyp from the determined distances; calculate an angle enclosing the polyp; and determine the width of the polyp from the calculated angle and determined distances.

10. A system according to claim 9, wherein the processing device is adapted to determine the height of polyps in the colon from a plurality of determined distances from the imaging capsule to the inner wall of the colon.

11. A system according to claim 9, wherein the radiation detector is coupled to the radiation emitter.

12. A system according to claim 9, wherein the radiation detector is independent from the radiation emitter.

* * * * *